United States Patent [19]

Sekino et al.

[11] Patent Number: 4,836,211
[45] Date of Patent: Jun. 6, 1989

[54] ULTRASONIC TREATMENT APPARATUS FOR PERFORMING MEDICAL TREATMENT BY USE OF ULTRASONIC VIBRATIONS

[76] Inventors: Naomi Sekino, 3-10-1, Motoyokoyama-cho, Hachioji-shi, Tokyo; Yoshio Tashiro, 4-23-3, Koyasu-machi, Hachioji-shi, Tokyo, both of Japan

[21] Appl. No.: 95,778

[22] Filed: Sep. 11, 1987

[30] Foreign Application Priority Data

Sep. 17, 1986 [JP] Japan ............................... 61-218453
Oct. 30, 1986 [JP] Japan ............................... 61-258854

[51] Int. Cl.⁴ .......................................... A61B 10/00
[52] U.S. Cl. ............................................ 128/662.05
[58] Field of Search ............. 128/660, 328, 305, 24 A, 128/660.05; 604/22

[56] References Cited

U.S. PATENT DOCUMENTS

| | | | |
|---|---|---|---|
| 3,830,240 | 8/1974 | Antonevich et al. | |
| 4,330,278 | 5/1982 | Martin | 128/24 A |
| 4,417,578 | 11/1983 | Banko | 604/22 |
| 4,425,115 | 1/1984 | Wuchinich | 604/22 |
| 4,516,398 | 5/1985 | Wuchinich | 604/22 |
| 4,526,571 | 7/1985 | Wuchinich | 604/22 |
| 4,609,368 | 9/1986 | Dotson, Jr. | 604/22 |
| 4,660,573 | 4/1987 | Brumbach | 128/328 |
| 4,698,058 | 10/1987 | Greenfield et al. | 128/328 |

Primary Examiner—Francis Jaworski
Assistant Examiner—George Manuel
Attorney, Agent, or Firm—Frishauf, Holtz, Goodman & Woodward

[57] ABSTRACT

A medical treatment apparatus utilizing ultrasonic vibrations includes an ultrasonic vibration generator having an ultrasonic oscillator with a first through-hole formed therein. A liquid supply device is communicated with one end of the first through-hole, and a second through-hole of a horn mounted on the ultrasonic vibration generator is communicated with the other end of the first through-hole. A transmission member for transmitting ultrasonic vibrations is connected to a front portion of the horn, and a tube member is arranged to surround the transmission member. A passage formed between the tube and transmission members is coupled to the second through-hole by coupling members, and the transmission member is slightly protruded from the distal end of the tube member. Therefore, a sufficient amount of the liquid supplied from the liquid supply device can be flowed through the passage.

5 Claims, 10 Drawing Sheets

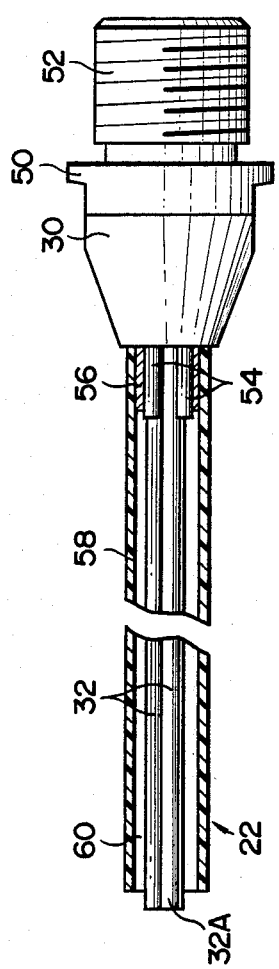
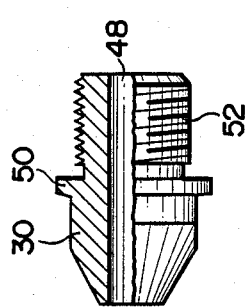
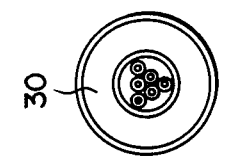
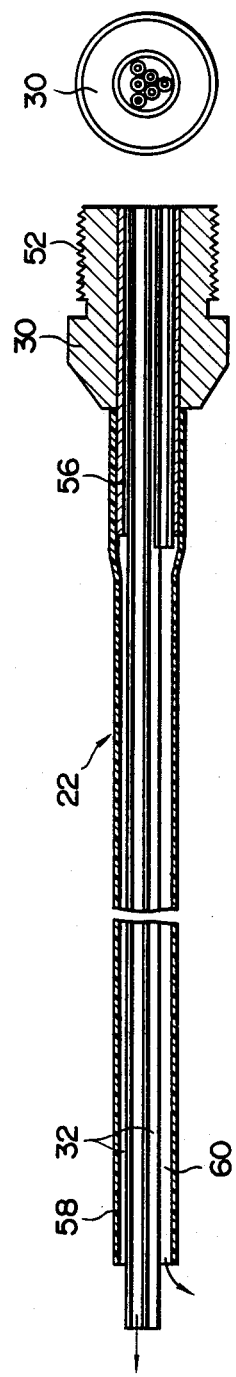
FIG. 4
FIG. 5
FIG. 7
FIG. 6

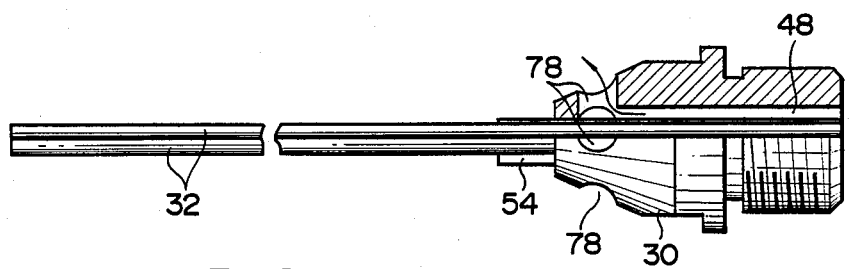
F I G. 11
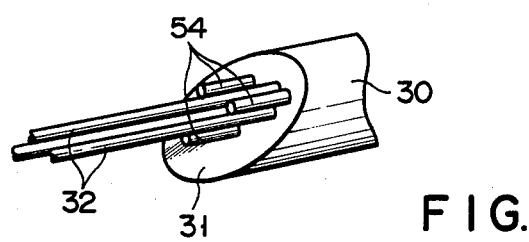
F I G. 12
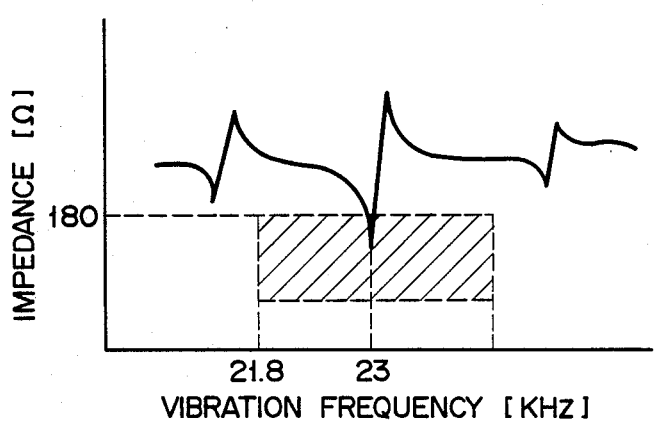
F I G. 13

ULTRASONIC TREATMENT APPARATUS FOR PERFORMING MEDICAL TREATMENT BY USE OF ULTRASONIC VIBRATIONS

BACKGROUND OF THE INVENTION

A. Field of the Invention

The present invention relates to an ultrasonic treatment apparatus for medical treatments, which is adapted to break up a ureteral stone or excise a thrombus by use of ultrasonic vibrations.

B. Description of the Prior Art

A typical ultrasonic treatment apparatus which breaks up a stone formed in a living body-especially in the ureter, the pelvis, a bile duct, or the like-by use of ultrasonic vibrations, is disclosed in, for example, Japanese Utility Model Disclosure (KOKAI) No. 60-55408 and U.S. Pat. No. 3,830,240. In this ultrasonic treatment apparatus, the vibration transmission member for transmitting ultrasonic vibrations has elasticity. In an ultrasonic treatment apparatus having another arrangement, disclosed in Japanese Utility Model Disclosure (KOKAI) No. 60-55409, the vibration transmission member is enclosed within a sheath, and a perfusate is able to flow through a space therebetween.

In the typical ultrasonic treatment apparatus, a longitudinal passage formed at the center of an oscillator is communicated with the through-hole of a pipe-like vibration transmission member, and cooling water flows through the passage to remove the heat generated by the vibrating of the oscillator.

However, if the vibration transmission member is made thinner to improve its elasticity, the cross-sectional area of the through-hole of the transmission member will be reduced, and hence satisfactory cooling cannot be provided, due to a consequent reduction in the flow rate of the perfusate.

In the ultrasonic treatment apparatus having the vibration transmission member enclosed within the sheath, if the cross-sectional area of the passage constituted by the space between the sheath and the transmission member is sufficiently maintained, the outer diameter of the overall insertion portion is enlarged, and hence the elasticity of the vibration transmission member is degraded.

A pipe made of a metal having elasticity is used as the vibration transmission member of the ultrasonic treatment apparatus disclosed in the Japanese Utility Model Disclosure (KOKAI) No. 60-55408. The vibration transmission member is inserted into a body cavity via a channel of an endoscope so as to be used for a medical treatment.

More specifically, the transmission member of the ultrasonic treatment apparatus is inserted into the channel through a forceps opening of the endoscope, and the distal end of the transmission member is made to protrude, from the distal end of the endoscope insertion portion, a length suitable for a treatment, this being normally 5 mm to 10 mm. Thereafter, the protruding vibration transmission member is pressed against a stone so as to break up the stone by means of the ultrasonic vibrations produced thereby.

In general, a forceps opening of the endoscope is obliquely formed with respect to the axis of the insertion portion, and a channel communicating with the forceps opening is bent inside an endoscope operation portion. For this reason, if the transmission member is inserted, from the forceps opening, into the channel, it comes into contact with the inner wall at a bent portion of the channel and hence is subjected to a straightening force.

The transmission member of the ultrasonic treatment apparatus alternately corresponds to loops and nodes of ultrasonic vibrations. For this reason, upon insertion of the transmission member into the endoscope channel, if the member portion corresponding to a loop of the vibration is brought into contact with the inner wall, the ultrasonic vibration is attenuated at this position, thereby disabling an effective treatment.

In order to eliminate the above problem, there is proposed an endoscope which is provided with a channel having no bent portion so that a forceps opening is formed substantially on an extention line of the axis of the insertion portion. In this endoscope, however, an eyepiece is deviated from the extension line of the axis. When the endoscope insertion portion is to be inserted into the body cavity, the operator must insert it while observing from the eyepiece. Therefore, if the eyepiece is deviated from the extension line of the axis of the insertion portion, operability is considerably degraded.

SUMMARY OF THE INVENTION

It is an object of the present invention to provide an ultrasonic treatment apparatus which is capable of sufficiently cooling a vibration transmission member or members even if a relatively thin vibration transmission member or members are mounted, while sufficiently supplying a perfusate into a body cavity, and which can efficiently utilize ultrasonic vibrations.

The above object of the present invention is achieved by the following ultrasonic treatment apparatus. More specifically, the ultrasonic apparatus comprises an ultrasonic vibration generator having an ultrasonic oscillator with a first through hole formed therein. A liquid supply device is communicated with one end of the first through-hole, and a second throughhole formed inside a horn for amplifying a vibration generated in the ultrasonic vibration generator is communicated with the other end of the first through-hole. A transmission member or members for transmitting the vibration are connected to the horn, and a tubular member is arranged to surround the outer surfaces of the transmission members. A passage formed between the tubular member and the transmission members is coupled to the second through-hole by coupling member, and the transmission members are slightly protruded from the distal end of the tubular member.

Thus, a sufficient amount of a cooling liquid or perfusate supplied from the liquid supply device flows through the passage so as to improve the cooling effect and supply a sufficient amount of the perfusate into the body cavity.

BRIEF DESCRIPTION OF THE DRAWINGS

FIG. 2 is a perspective view showing an ultrasonic treatment system in which the ultrasonic treatment apparatus according to the first embodiment of the present invention is incorporated;

FIGS. 3 and 4 are front and partially cutaway side views, respectively, showing insertion and connecting portions of the ultrasonic treatment apparatus according to the first embodiment;

FIG. 5 is a partially cutaway side view of the connecting portion shown in FIG. 4;

FIGS. 6 and 7 are longitudinal sectional and rear views, respectively, showing the insertion and connecting portions of the ultrasonic treatment apparatus of the first embodiment;

FIG. 11 is a partially cutaway view showing a modification of the connecting portion according to the first embodiment;

FIG. 12 is a perspective view showing another modification of the connecting portion according to the first embodiment;

FIG. 13 is a graph showing a relationship between vibration frequency and impedance in typical vibration transmission members;

DETAILED DESCRIPTION OF THE PREFERRED EMBODIMENTS

Figure 1:
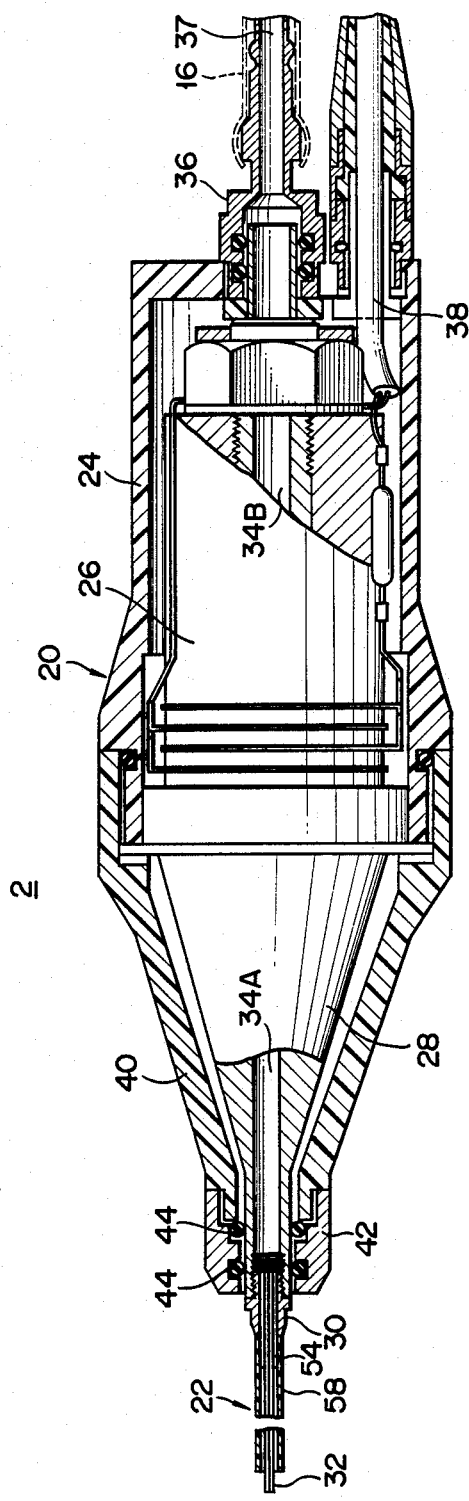
FIG. 1 is a partially cutaway side view showing a first embodiment of an ultrasonic treatment apparatus according to the present invention.

An embodiment of the present invention will be described in detail with reference to the accompanying drawings hereinafter.

In FIGS. 1 to 8, a first embodiment of an ultrasonic treatment apparatus according to the present invention is disclosed. An ultrasonic treatment system shown in FIG. 2 comprises ultrasonic treatment apparatus 2, endoscope 3, and power supply device 6. Insertion portion 22 of ultrasonic treatment apparatus 2 is inserted into channel 5 formed in insertion portion 4 of endoscope 3, and power supply device 6 is connected to handling portion 20 of ultrasonic treatment apparatus 2. Liquid supply unit 9 and foot switch 10 are connected to power supply device 6. Perfusion pump 11 of liquid supply unit 9 pumps a perfusion liquid from tank 12 via pumping tube 14, and can supply it to ultrasonic treatment apparatus 2 through liquid supply tube 16. Ultrasonic treatment apparatus 2 can be turned on/off by foot switch 10.

Figures 2, 3:
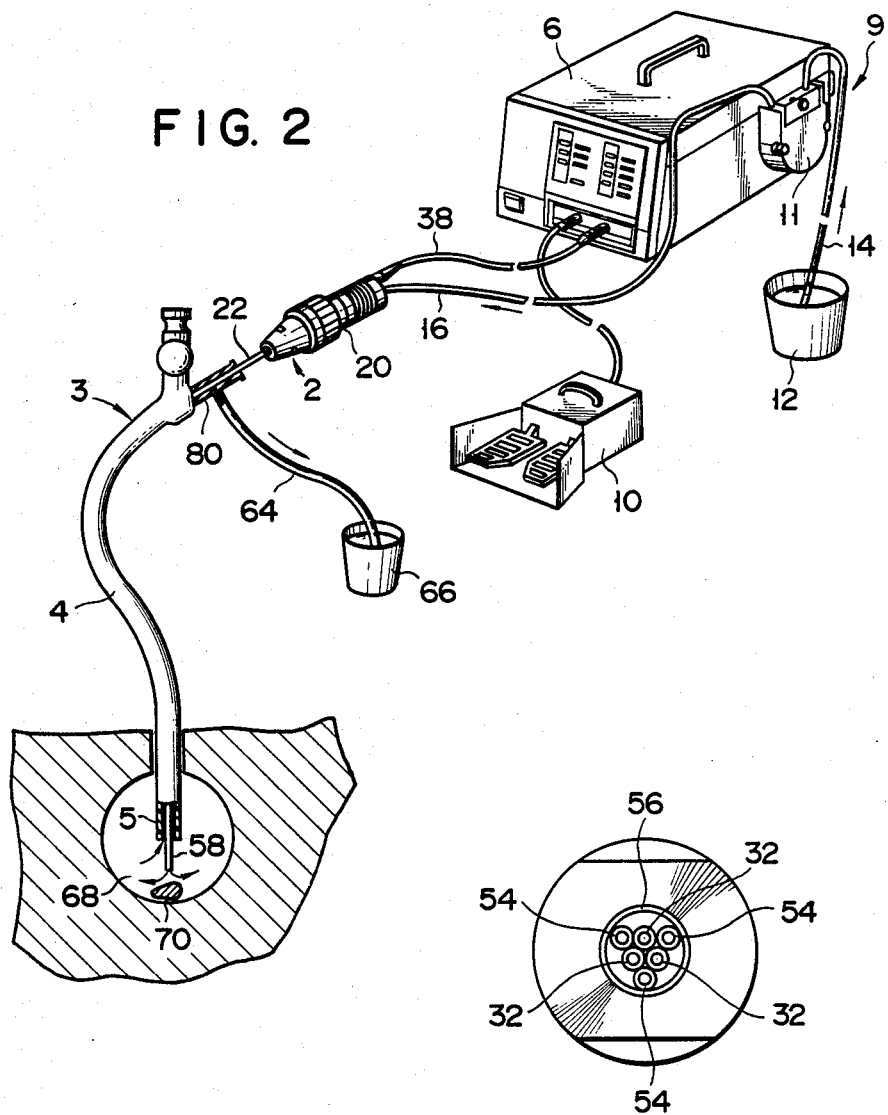
Figure 8:
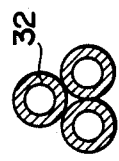
FIG. 8 is a cross-sectional view of vibration transmission members shown in FIG. 6.

FIG. 1 shows a structure of ultrasonic treatment apparatus 2 in detail. Ultrasonic treatment apparatus 2 comprises handling portion 20 and insertion portion 22, and Langevin type oscillator 26 is stored in case 24 of handling portion 20. Horn 28 is coupled to a distal end portion of oscillator 26, and vibration transmission members 32 are detachably connected to a distal end portion of horn 28 by connecting member 30. Through holes 34A and 34B constituting a passage, through which the perfusion liquid for cooling the oscillator and perfused in a body cavity is flowed, are coaxially formed at the centers of oscillator 26 and horn 28. Through holes 34A and 34B are connected to through hole 37 of connecting mouthpiece 36 formed to extend through a rear wall portion of case 24. Furthermore, liquid supply tube 16 is connected to connecting mouthpiece 36. Power cord 38 of Langevin type oscillator 26 is connected to power supply device 6, as shown in FIG. 2. Cover 40 for covering horn 28 is mounted on the distal end of case 24, and cap 42 is mounted on the distal end of cover 40. O-ring 44 for providing a seal is mounted on an inner surface of cap 42, and pressed against the periphery of a distal end portion of horn 28.

FIGS. 3 to 8 show insertion portion 22 in detail. As shown in FIGS. 4 and 6, insertion portion 22 comprises three vibration transmission members 32 each having a thin pipe-like shape, and connecting member 30 is adhered to proximal end portions of vibration transmission members 32 by brazing or the like. Vibration transmission member 32 is formed by an ultra elastic alloy such as Ti-Ni, has a straight tubular shape, and can be ultra-elastically bent. As shown in FIG. 5, connecting member 30 has hollow portion 48, flange 50 is formed around an intermediate portion of connecting member 30, and male threads 52 are formed around its proximal end portion. Male threads 52 can be screwed in and fixed to the distal end portion of horn 28.

Vibration transmission members 32 and a plurality of perfusion pipes 54 are bundled with each other, inserted into pipe member 56 mounted in hollow portion 48 of connecting member 30, and brazed in such a manner that a brazing material is filled into a space between the inner wall of pipe member 56 and the outer surfaces of transmission members 32 and perfusion pipes 54. More specifically, although the outer surfaces of vibration transmission members 32 and perfusion pipes 54 are sealed by the brazing material, communication of the internal holes thereof with through hole 34A is maintained. The outer surfaces of vibration transmission members 32, substantially from the proximal ends to the distal ends thereof, are surrounded by soft tube 58, and only distal end portions 32A of vibration transmission members 32 are slightly protruded from the distal end of tube 58. A proximal end portion of tube 58 is watertightly mounted on the outer surface of pipe member 56 mounted on connecting member 30. Each perfusion pipe 54 is constituted by a relatively short pipe, and caused to commuunciate with perfusion passage 60 formed between vibration transmission members 32 and tube 58.

Insertion portion 22 of ultrasonic treatment apparatus 2 having the above-described arrangement is inserted into channel 5 of endoscope insertion portion 4, as shown in FIG. 2. Endoscope 3 has mouthpiece 80, and drain tube 64 communicating with channel 5 of insertion portion 4 is connected to mouthpiece 80. The distal end of drain tube 64 is inserted into waste liquid tank 66.

Accordingly, the perfusion liquid can be drained from the body cavity through channel 5.

An operation of the ultrasonic treatment apparatus according to the present invention will be described.

When ultrasonic treatment apparatus 2 is to be used, as shown in FIG. 2, power supply device 6 is connected to ultrasonic treatment apparatus 2, and insertion portion 22 is introduced into body cavity 68 via channel 5 of endoscope insertion portion 4. Then, perfusion pump 11 is actuated by operating foot switch 10 so as to pump a perfusion liquid from tank 12 via pumping tube 14, and supply the perfusion liquid to body cavity 68 via tube 16 and through holes 34A, 34B of ultrasonic treatment apparatus 2. More specifically, the perfusion liquid is supplied to hollow portion 48 of connecting member 30 via through hole 37 of connecting mouthpiece 36 and through holes 34A, 34B formed inside oscillator 26 and horn 28, and supplied to a distal end portion of insertion portion 22 via an internal hole of each vibration transmission member 32 and each perfusion pipe 54. The perfusion liquid flowing through each perfusion pipe 54 is flowed through perfusion passage 60 formed between vibration transmission members 32 and tube 58, and flowed into body cavity 68 from the distal end of member 32. Similarly, the perfusion liquid flowing through the internal holes of vibration transmission members 32 is flowed into body cavity 68 from the distal end of member 32. At the same time, oscillator 26, horn 28 and vibration transmission members 32 of ultrasonic treatment apparatus 2 are cooled by the perfusion liquid flowing through the passage.

The perfusion liquid flowed into body cavity 68 is drained to waste liquid tank 66 via channel 5 of endoscope insertion portion 4 and drain tube 64.

As described above, body cavity 68 is observed from endoscope 3, while body cavity 68 is always perfused with a liquid, the distal ends of vibration transmission members 32 are pressed against a stone to be treated, e.g., stone 70, and oscillator 26 is actuated by operating foot switch 10. As a result, ultrasonic vibrations generated by oscillator 26 are amplified by horn 28, transmitted to vibration transmission members 32, and then transmitted to stone 70, thereby breaking stone 70.

Since each vibration transmission members 32 has a small diameter, a flow rate of perfusion liquid passing through its internal hole is limited. However, the perfusion liquid can be supplied also through perfusion passage 60 formed inside external tube 58, and the overall flow rate can be increased in proportion to the inner diameter and number of perfusion pipes 54. Therefore, a sufficiently high flow rate of the perfusion liquid can be maintained.

Figure 10:
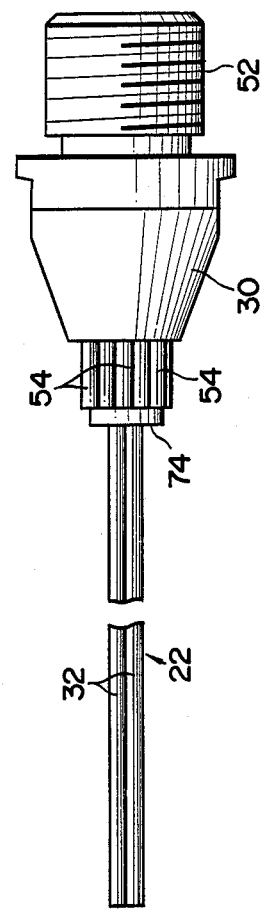
FIGS. 9 and 10 are front and side views, respectively, showing a modification of a perfusion pipe according to the first embodiment.
Figure 9:
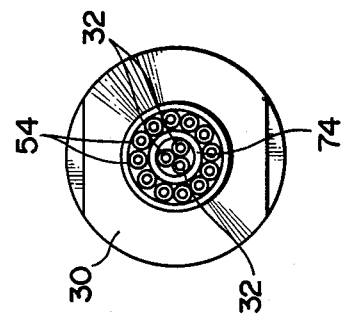

FIGS. 9 and 10 show a modification of the perfusion pipes.

In this modification, a plurality of, e.g., three vibration transmission members 32 are inserted into second pipe member 74, and adhered thereto by brazing or the like. A plurality of perfusion pipes 54 are arranged around second pipe member 74, and each perfusion pipe 54 is fitted in hollow portion 48 of connecting member 30 and adhered thereto by brazing or the like.

Other arrangements are similar to those of the first embodiment, and hence will be omitted.

In FIG. 11, a modification of the connecting member according to the first embodiment is disclosed.

In this modification, a plurality of water supply openings 78 are formed in the outer surface portion of a distal end portion of connecting member 30, and each water supply opening 78 is caused to communicate with hollow portion 48. Furthermore, when a proximal end portion of tube 58 (not shown) is mounted on connecting member 30, each water supply opening 78 is caused to communicate with perfusion passage 60 formed inside tube 58. In addition to the internal holes of vibration transmission members 32 and perfusion pipes 54, water supply openings 78 can communicate with perfusion passage 60. Therefore, a sufficiently high flow rate of perfusion liquid can be maintained.

In FIG. 12, another modification of the connecting member is disclosed.

In this modification, connecting member 30 has inclined distal end face 31, and vibration transmission members 32 and perfusion pipes 54 are protruded forward from distal end face 31.

Note that the number of vibration transmission members is not specifically limited. Furthermore, an adequate number of perfusion pipes are preferably arranged around the vibration transmission members in accordance with the outer diameter and number of the transmission members so as to sufficiently cool them.

Figure 14:
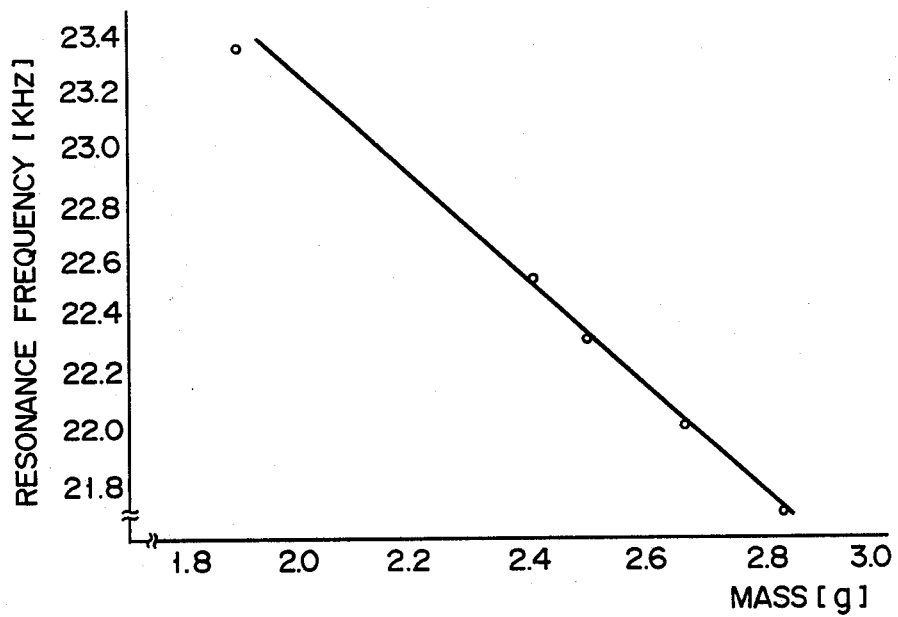
FIG. 14 is a graph showing a relationship between mass and resonant frequency in the typical connecting member.
Figure 15:
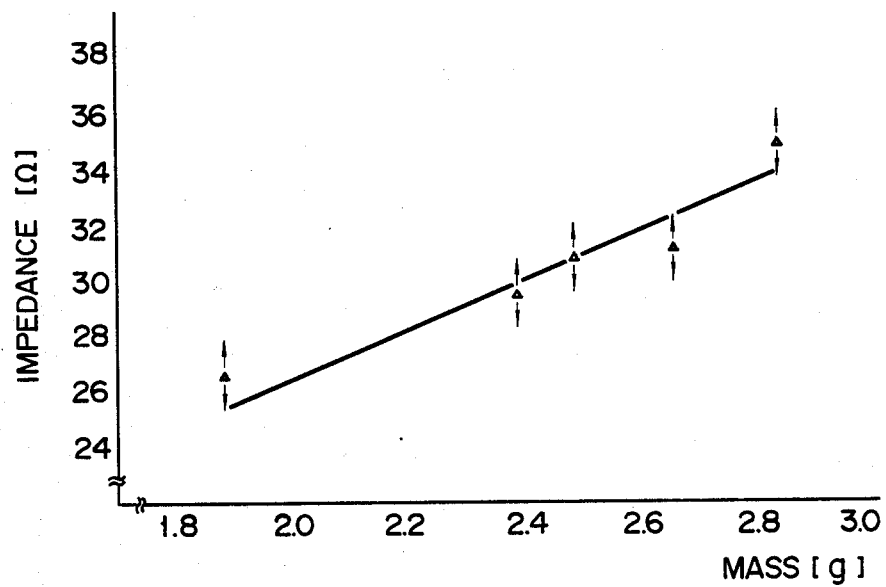
FIG. 15 is a graph showing a relationship between mass and impedance in the typical connecting member.

In general, vibration frequency vs. impedance characteristics of a vibration transmission member can be shown as in a graph of FIG. 13. The oscillator is designed to be oscillated at, e.g., 22 KHz or more and 200 $\Omega$ or less. The ranges of vibration frequency and impedance are set in the above manner so that the oscillator does not operate except at a resonant frequency near 23 KHz. A vibration transmission member which has a relatively large outer diameter and rigidity is oscillated within the above ranges, but a vibration transmission member which has the same outer diameter and softness is not oscillated because its resonant frequency and impedance fall outside the above ranges. the reason for this is that a mass-ratio of the connecting member and the soft vibration transmission member is larger than that of the connecting member and the rigid vibration transmission member. Thus, as in the ultrasonic treatment apparatus according to the present invention, the pipe member is arranged around the vibration transmission members, or the holes are formed in the connecting member so as to reduce the mass of the connecting member of an oscillation portion. As a result, as shown in FIGS. 14 and 15, the resonant frequency is increased, and the impedance is decreased, thereby setting the optimal frequency and impedance.

In general, if a sectional area of each vibration transmission member is greatly changed upon transmission of vibrations from the connecting member to the vibration transmission members, a stress is partially increased, resulting in a breakage in a pipe. In the ultrasonic treatment apparatus according to the present invention, however, since the pipe member is arranged around the vibration transmission members, a sectional area of the connecting member can be reduced. Therefore, a ratio of sectional areas of the connecting member and the vibration transmission members can be reduced, thereby reducing generation of local stress.

An ultrasonic treatment apparatus according to a second embodiment will be described with reference to FIGS. 16 to 18.

Figure 16:
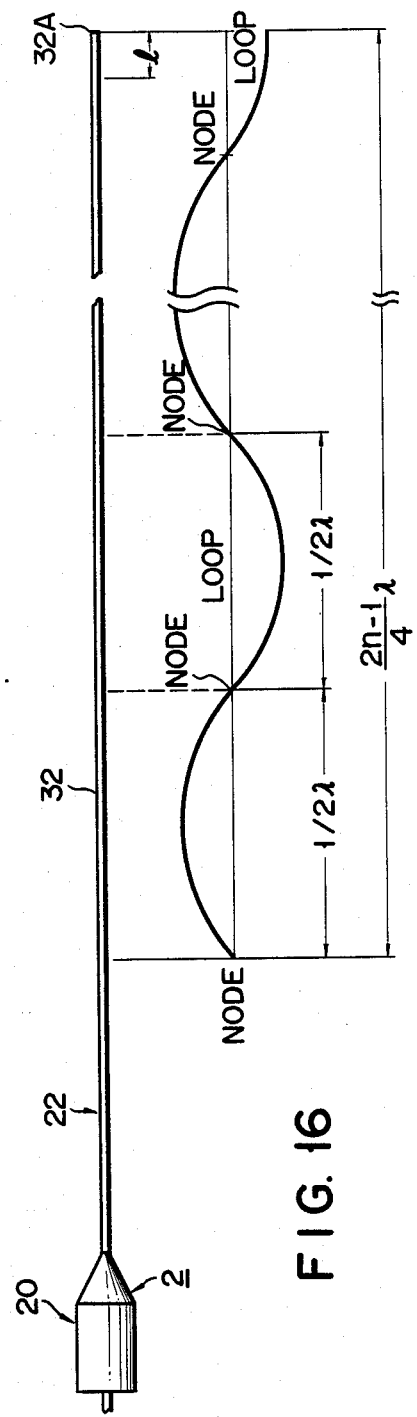
FIG. 16 is a schematic side view showing a second embodiment according to the present invention with a vibration waveshape.

FIG. 16 schematically shows ultrasonic treatment apparatus 2 according to the second embodiment. Ultrasonic treatment apparatus 2 is constituted by handling portion 20 incorporating an ultrasonic oscillator, and insertion portion 22 having transmission member 32 for transmitting ultrasonic vibrations. In order to provide elasticity to transmission member 32, transmission member 32 is constituted by, for example, a plurality of relatively thin stainless steel pipes are bundled together, and the resultant structure is covered with a thin resin tube. Furthermore, as shown in FIG. 16, transmission member 32 has a length such that the maximum amplitude of vibration can be obtained at distal end 32A. Loops and nodes of vibration respectively having cycles of $n\lambda/2$ and $(2n-1)\lambda/4$ alternately appear from distal end 32A of transmission member 32 to handling portion 20. Wavelength $\lambda$ of an ultrasonic wave transmitted through transmission member 32 is defined by a vibration frequency generated by the ultrasonic oscillator (not shown). In this embodiment, since the ultrasonic oscillator to be oscillated at 32 KHz and transmission member 32 constituted by a stainless pipe are used, wavelength $\lambda$ is set to about 150 mm.

Figure 17:
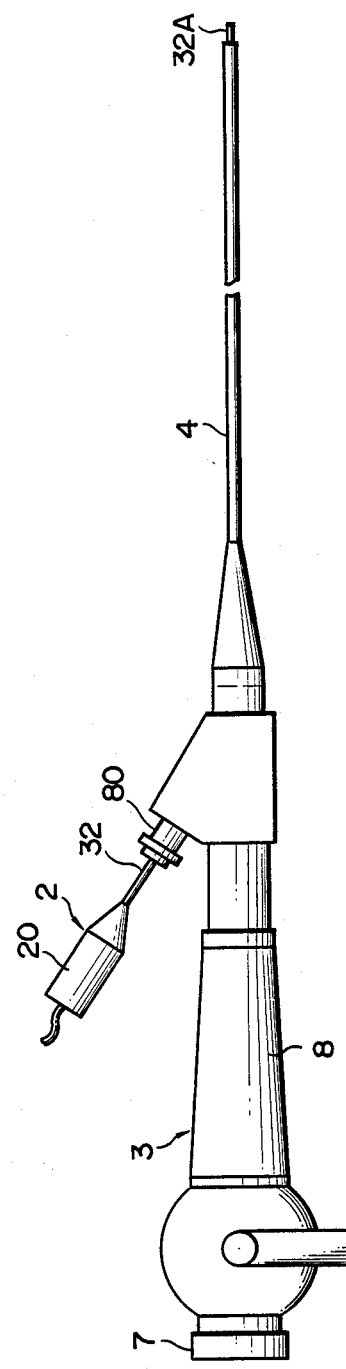
FIG. 17 is a side view showing an endoscope in which the ultrasonic treatment apparatus in FIG. 16 is incorporated.
Figure 18:
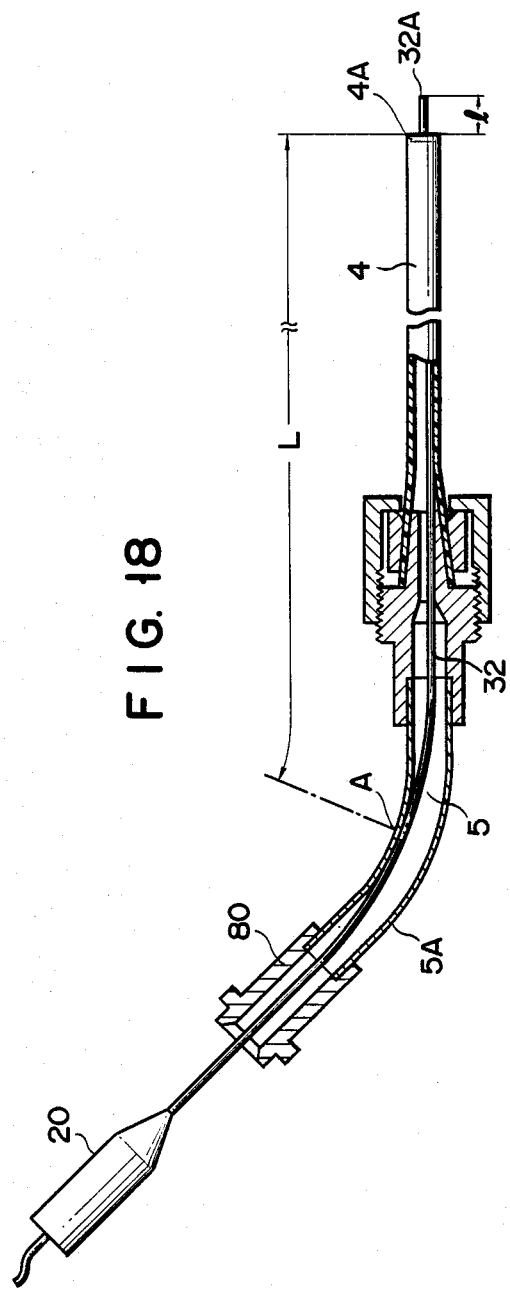
FIG. 18 is a partially cutaway side view schematically showing the ultrasonic treatment apparatus according to the second embodiment, which is inserted into an endoscope channel.

FIGS. 17 and 18 show ultrasonic treatment apparatus 2 wherein vibration transmission member 32 is inserted into channel 5 of endoscope insertion portion 4, and also show endoscope 3. Endoscope 3 comprises insertion portion 4, operation portion 8, eyepiece 7, and forceps opening 80 connected to forceps channel 5. As shown in FIG. 18, transmission member 32 of ultrasonic treatment apparatus 2 is inserted into channel 5 from forceps opening 80 of endoscope 3, and distal end 32A of transmission member 32 is protruded from distal end portion 4A of endoscope insertion portion 4 by a length suitable for breaking a stone in the body cavity, i.e., length L=5 mm to 10 mm. If the length of the protruded portion of end portion 32A is set to an optimum value, the stone can be effectively broken, with end portion 32A being observed. In this case, an intermediate portion of transmission member 32 is brought into contact with the inner wall of bent portion 5A of channel 5 at contact portion A, and transmission member 32 is pressed against the inner wall of bent portion 5A by a straightening force of transmission member 32.

The lengths of transmission member 32 and endoscope insertion portion 4 are determined such that contact portion A of transmission member 32 is set at a $(2n-1)\lambda/4$ position from distal end 32A of transmission member 32 in this state. More specifically, if the length from distal end portion 4A of insertion portion 4 to contact portion A is L, the lengths of transmission member 32 and endoscope insertion portion 4 are determined to satisfy:

$$L + 1 = (2n-1)\lambda/4$$

Therefore, if transmission member 32 is oscillated in this state, since contact portion A is positioned at a portion near a node of ultrasonic vibration, a loss of vibration energy caused by friction between transmission member 32 and the channel inner wall at contact portion A can be reduced, and hence the ultrasonic vibration can be efficiently transmitted to distal end 32A of transmission member 32.

Figure 19:
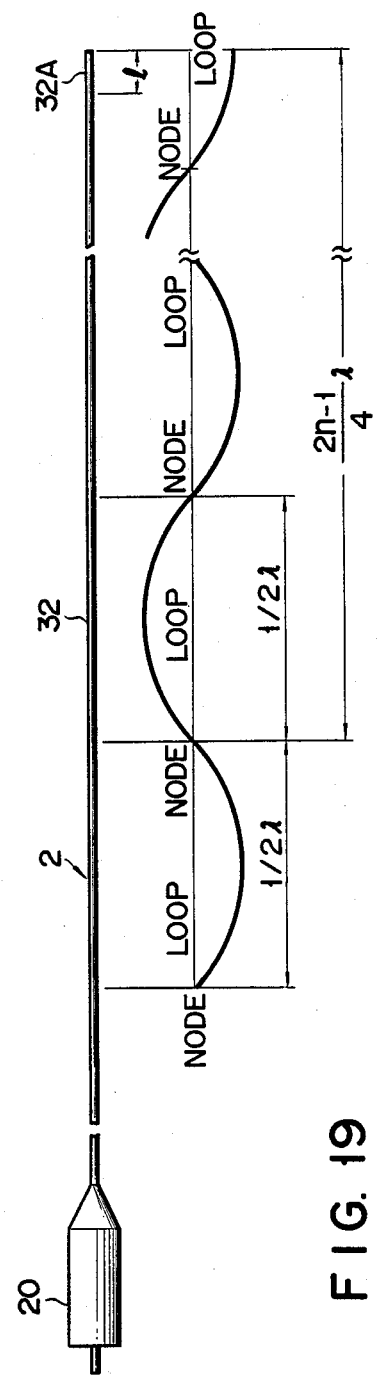
FIG. 19 is a schematic side view showing a modification of the ultrasonic treatment apparatus according to the second embodiment with a vibration waveshape.
Figure 20:
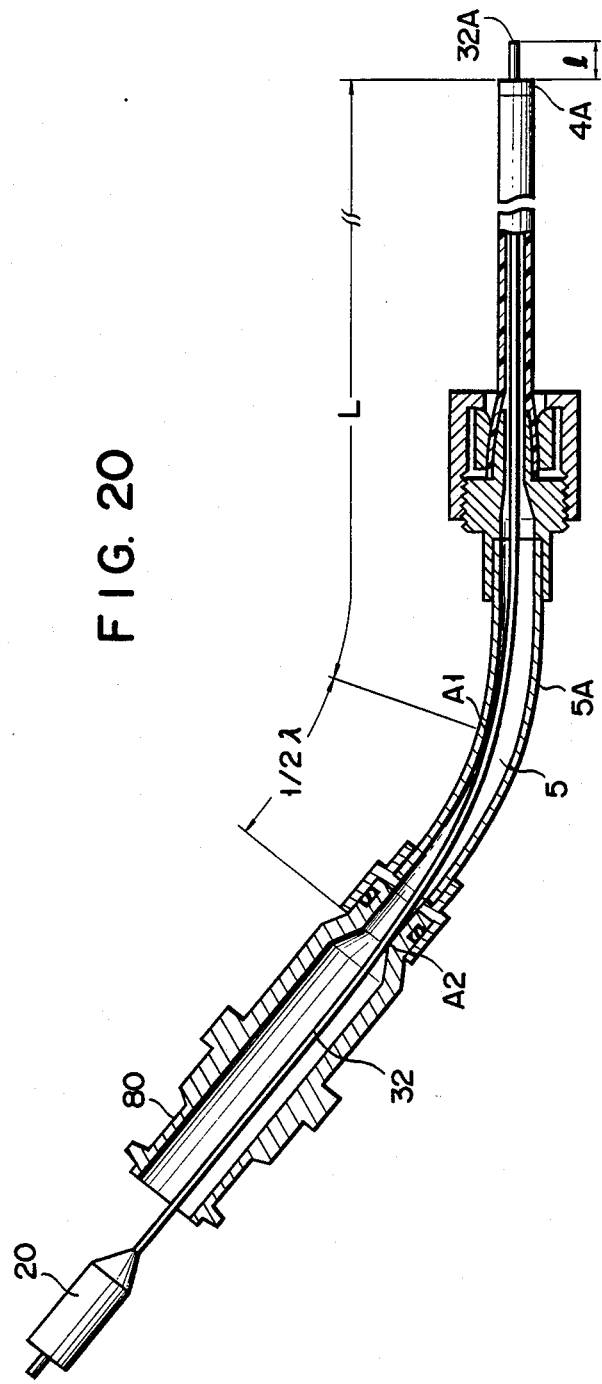
FIG. 20 is a partially cutaway view schematically showing the ultrasonic treatment apparatus according to the modification of the second emobidment, which is inserted into the endoscope channel.

In FIGS. 19 and 20, a modification of the ultrasonic treatment apparatus according to the second embodiment is disclosed. In this modification, transmission member 32 is in contact with the inner wall of channel 5 of endoscope 3 at first and second contact portions A1 and A2. In the ultrasonic treatment apparatus according to this modification, the lengths of transmission member 32 and endoscope insertion portion 4 are determined such that first contact portion A1 is set at a $(2n-1)\lambda/4$ position from distal end 32A of transmission member 32, and second contact portion A2 is set at a $\lambda/2$ position from first contact portion A1. Therefore, in this modification, effects similar to those in the aforementioned embodiment can be obtained.

Figure 21:
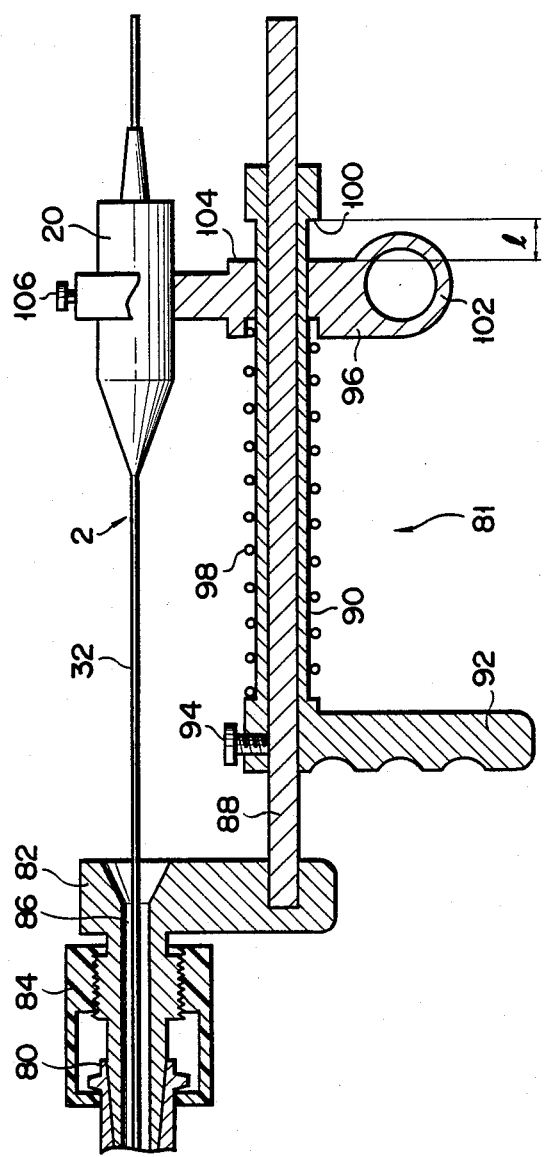
FIG. 21 is a partially cutaway side view of an auxiliary operation assembly in which the ultrasonic treatment apparatus is incorporated.

In FIG. 21, auxiliary operation assembly 81 of ultrasonic treatment apparatus 2 used in the second embodiment and the modification is disclosed. Auxiliary operation assembly 81 has connecting metal member 82, which is detachably mounted on forceps opening 80 of endoscope 3 by fixing ring 84. Furthermore, connecting metal member 82 has probe insertion passage 86 through which transmission member 32 of ultrasonic treatment apparatus 2 is inserted into channel 5, and slide shaft 88 is mounted on a proximal end portion of connecting metal member 82 to be parallel to probe insertion passage 86. Tubular member 90 is mounted on slide shaft 88 to be slidable forward and backward. Front grip 92, which is gripped by operator's fingers upon operation, is formed on a distal end portion of tubular member 90. Slide shaft 88 can be fixed to tubular member 90 by set screw 94, and operation lever 96 is slidably mounted on the outer surface of tubular member 90. Operation lever 96 is biased by coil spring 98 toward stopper 100 formed on a proximal end portion of tubular member 90. Furthermore, mount 104 and rear grip 102 which is hooked by the operator's finger are formed on operation lever 96, and handling portion 20 can be fixed to mount 104 by set screw 106.

When a treatment for a stone is performed by ultrasonic treatment apparatus 2 using auxiliary operation assembly 81 with the above-described arrangement, auxiliary operation assembly 81 is mounted on forceps opening 80 of endoscope 3. Then, transmission member 32 of ultrasonic treatment apparatus 2 is inserted into channel 5 via probe insertion passage 86 of auxiliary operation assembly 81, and handling portion 20 is fixed to mount 104 of operation lever 96. Note that in this case, distal end portion 32A of transmission member 32 is stored inside distal end portion 4A of endoscope insertion portion 4. In this state, distal end portion 4A of endoscope insertion portion 4 is moved near the stone, the operator's finger is put through rear grip 102 of operation lever 96, and operation lever 96 is moved toward front grip 92 so that distal end portion 32A of transmission member 32 is protruded from distal end portion 4A of endoscope insertion portion 4 by length . When the ultrasonic oscillator of handling portion 20 is oscillated after distal end portion 32A of transmission member 32 is protruded by length l, distal end portion 32A is set at a position corresponding to a loop of vibration, while contact portion A of channel 5 is set at a position near a node of vibration, i.e., in the range of $\pm\lambda/8$ with respect to the node as the center, thereby transmitting the vibration to the distal end without attenuating it. Furthermore, even transmission member 32 having a relatively large length from forceps opening 80 to handling portion 20 can be easily operated using auxiliary operation assembly 81.

What is claimed is:
1. A medical treatment apparatus for use in combination with an endoscope including an insertion portion having a channel, said apparatus comprising:
   ultrasonic vibration generation means including an oscillator having means for defining a first through-hole;
   liquid supply means in communication with one end of the first through-hole;

a horn having means for defining a second through-hole, said second through-hole being in communication with the other end of the first through-hole, said horn being coupled to, and adapted to amplify vibration generated by, said ultrasonic vibration generation means;

a transmission member connected to said horn for transmitting the amplified vibration, said transmission member having means defining an internal hole extending axially therethrough and in communication with said second through-hole for accommodating liquid flow from the liquid supply means in an outward direction;

a tubular member surrounding said transmission member, thus defining a passage therebetween, and said transmission member protruding from a distal end of said tubular member; and coupling means for communicating said passage with the second through-hole for supplying liquid from the liquid supply means to flow through said passage in said outward direction.

2. A treatment apparatus according to claim 1, wherein said transmission member comprises a plurality of thin tubular members each having means for defining an internal hole connected to the second through-hole.

3. A treatment apparatus according to claim 2, wherein said coupling means comprises:

a plurality of short tubes positioned at intervals around an outer periphery of said transmission member; and a connecting member having means defining a through-hole in which proximal end portions of said transmission member and said short tubes are stored, and which is detachably mounted on said horn.

4. A treatment apparatus according to claim 3, wherein said connecting member includes means defining a water supply opening formed on a distal end portion thereof and adapted to communicate with said second through-hole.

5. A treatment apparatus according to claim 1, wherein said transmission member is received in the channel of the insertion portion of said endoscope, which has a bent portion, and a distal end portion of said transmission member protrudes from the distal end of said insertion portion by a predetermined length, and respective lengths of said transmission member and the insertion portion of said endoscope are such that when said transmission member is oscillated at a predetermined resonant frequency, a portion of said transmission member which engages an inner wall of said channel at said bent portion substantially coincides with a node of vibration.

* * * * *

UNITED STATES PATENT AND TRADEMARK OFFICE
CERTIFICATE OF CORRECTION

PATENT NO. : 4,836,211

DATED : June 6, 1989

INVENTOR(S) : SEKINO et al

It is certified that error appears in the above-identified patent and that said Letters Patent is hereby corrected as shown below:

In the title page below "Inventors", add

--Assignee: Olympus Optical Co., Ltd.
Tokyo, Japan--.

Signed and Sealed this

Seventeenth Day of April, 1990

Attest:

HARRY F. MANBECK, JR.

*Attesting Officer*  *Commissioner of Patents and Trademarks*